United States Patent [19]

Kalopissis et al.

[11] 4,124,632

[45] Nov. 7, 1978

[54] SURFACE ACTIVE AGENTS

[75] Inventors: Gregoire Kalopissis, Paris; Guy Vanlerberghe, Mitry-Mory, both of France

[73] Assignee: Societe Anonyme dite l'Oreal, Paris, France

[21] Appl. No.: 758,675

[22] Filed: Jan. 12, 1977

Related U.S. Application Data

[60] Division of Ser. No. 134,390, Apr. 15, 1971, Pat. No. 4,020,155, which is a continuation-in-part of Ser. No. 576,852, Sep. 2, 1966, abandoned.

[30] Foreign Application Priority Data

Sep. 6, 1965 [LU] Luxembourg .............................. 49442

[51] Int. Cl.² ................... C07C 101/24; A61K 31/205
[52] U.S. Cl. ................................................ 260/501.13

[58] Field of Search ..................................... 260/501.13

[56] References Cited

U.S. PATENT DOCUMENTS

| | | | |
|---|---|---|---|
| 3,113,026 | 12/1963 | Sprung ............................ | 260/501.13 |
| 3,360,550 | 12/1967 | Cowen et al. .................... | 260/501.13 |
| 3,920,731 | 11/1975 | Naik ................................ | 260/501.13 |

*Primary Examiner*—James O. Thomas, Jr.
*Assistant Examiner*—G. T. Breitenstein

[57] ABSTRACT

New amphoteric compounds which contain two basic groups, at least one of which is a quaternary ammonium group, and an anionic group of the carboxylic type and one or two lipophile chains. These compounds have excellent cationic characteristics while being less, and in some cases non-irritating to the mucous membrane of the eye.

3 Claims, No Drawings

SURFACE ACTIVE AGENTS

This application is a division of Ser. No. 134,390 filed Apr. 15, 1971, which is a continuation-in-part application of Ser. No. 576,852 filed Sept. 2, 1966.

This invention relates to new surface-active agents which may be advantageously used in the cosmetic field. When so used, these new surface-active agents offer substantial advantages over those heretofore known.

Anionic surface-active agents have been used for a long time in shampoos for the human hair. Such agents have little tendency to irritate the scalp or the mucous membranes, but by reason of their chemical structure, have no affinity for keratinic fibres.

For this reason, it has become more and more common to use for cosmetic purposes cationic surface-active agents such as quaternary ammoniums which, because of their natural affinity for keratinic fibres, have a greater "conditioning" effect, but which, in spite of all the efforts and improvements heretofore made, are nevertheless somewhat irritating, especially to the mucous membrane of the eye.

The compounds according to the invention are amphoteric and comprise within each molecule two basic groups, at least one of which is a quaternary ammonium group, together with an anionic group of the carboxylic type, as well as one or two lipophile chains. These compounds have the great advantage of possessing the same conditioning properties as cationic compounds, while being less or even non-irritating to the mucous membrane of the eye.

It is accordingly the object of the present invention to provide a new article of manufacture which consists of a compound essentially characterized by the fact that it responds to the following formula:

$$\left[ \overset{+}{A} - CH_2CONH - (CH_2)_n - B \right] X^-$$

in which:

A represents a nitrogenous tertiary base which consists of either:
an aliphatic tertiary amine having the formula:

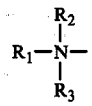

in which:

$R_1$ represents a methyl or an alkyl or alkenyl radical and mixtures thereof having 6 to 18 carbon atoms, and
$R_2$ and $R_3$, which may be identical or different, each represent an alkyl radical, or an hydroxy alkyl radical comprising 1 to 3 carbon atoms (for example a methyl, ethyl, hydroxy-ethyl, or 2-hydroxy propyl radical).
or a nitrogenous heterocyclic tertiary base.
n represents a whole number equal to 2 or 3,
B represents either:
the group:

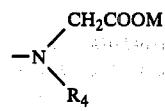

or the group:

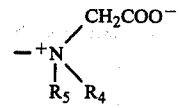

in which $R_4$ represents either an alkyl or alkenyl radical and mixtures thereof having 6 to 18 carbon atoms, or an alkyl or a hydroxy alkyl radical having 1 to 3 carbon atoms; $R_5$ represents a lower alkyl comprising 1 to 3 carbon atoms; and M represents an alkaline metal such as sodium or potassium.

X represents an anion, preferably a halide.

In one embodiment of the invention, the nitrogenous heterocyclic tertiary base which is represented by A in the above formula consists of either an N-alkyl-morpholine, or an N-hydroxy-alkyl morpholine, or an imidazoline.

The most useful imidazoline is one having a lipophile chain with 5 to 17 carbon atoms and which is obtained by the condensation of fatty acids $C_6$-$C_{18}$ carbon atoms on diamines which may be hydroxy-alkylized. Those fatty acids found in copra (see Fieser & Fieser, 3rd Ed. P. 408) are particularly referred to.

Compounds according to the invention having a single lipophile chain in their molecule have cleansing and foaming properties which are very valuable in the cosmetic field.

Compounds according to the invention having two lipophile chains in their molecule, when placed in aqueous solution, have thickening and gelling properties and may also be used very advantageously in cosmetics. The lipophile chains, of course, being the fatty acid aliphatic chains with 5–18 C. atoms.

Another object of the present invention is to provide a process for preparing compounds such as those hereinbefore defined, said process being essentially characterized by the fact that a betaine ester is aminolyzed by an alkylene diamine having a primary amine function and a secondary or tertiary amine function. The secondary or tertiary amine function of the compound thus obtained is alkylized by an alkaline salt of a monohalogen acetic acid or by a lower ester of such an acid, in which case the intermediate amino or ammoni-ester is then saponified.

The betaine esters used in the above process are formed by quaternizing a nitrogenous tertiary base by a lower ester of a halogenated acetic acid, according to a known process.

Tertiary bases which are particularly useful in obtaining the necessary betaine esters are the tertiary amines which may or may not include a substituent, which is a fatty chain having 5 to 18 carbon atoms.

Among these tertiary bases are, for example, the dimethylated fatty amines formed from mixtures of natural fatty acids. These amines may be first fractionated by distillation.

Tertiary amines such as trimethylamine, N,N-dimethylethanolamine, N,N-dimethylisopropanolamine and N-hydroxyethylmorpholine may also be used as tertiary bases.

If one of the substituents of the tertiary amine used in a hydroxyalkyl radical, the betaine ester may also consist of a lactone.

When, as indicated above, the nitrogenous tertiary base used to form the betaine ester is an imidazoline having the formula:

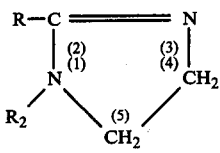

in which:

R represents a lipophile chain, namely an alkyl or alkenyl radical and mixtures thereof derived from fatty acids and comprising 5-17 carbon atoms, and mixtures thereof;

$R_2$ represents an alkyl radical or a lower hydroxy alkyl radical having 1-3 C. atoms, the quaternization reaction gives rise to a compound which has been shown invariably, especially in the patent literature, with both alkyl groups on the same nitrogen atom and the compound has been represented by the following formula:

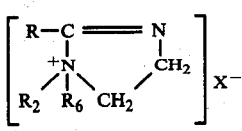

However, the compound is now commonly represented by the following resonance forms:

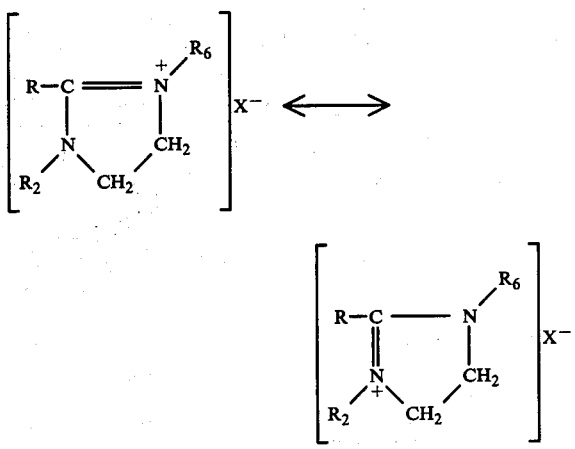

formulae in which $R_1$, $R_2$ and X have the same meaning, $R_6$ represents the radical —$CH_2CONH$—$(CH_2)_n$—B in which n and B have the same meaning as above mentioned.

Among the imidazolines which may be used according to the invention, the 1-hydroxy ethyl-2-alkyl imidazolines obtained by condensing fatty acids with N-(hydroxyethyl)-ethylenediamine are particularly useful as raw materials.

The aminolysis of the betaine esters according to the invention may be carried out in a particularly advantageous manner by using the following alkylenediamines, although this list is in no way exhaustive: N-(hydroxyethyl)-ethylene diamine, 3-N,N-dimethylamino-propylamine, 2-N,N-diethylamino ethylamine and those trimethylenediamines monosubstituted by an alkyl radical having 6 to 18 carbon atoms.

These diamines can be obtained by cyanoethylizing a long-chain primary amine, then hydrogenating aminonitrile.

Another object of the present invention is to provide the new article of manufacture which consists of a cosmetic composition essentially characterized by the fact that it contains at least one compound such as those described above.

The concentration of the compound in the cosmetic composition is generally comprised between 1 to 10% by weight.

The cosmetic omposition can take the form of a tinctorial composition for hair containing further to the compound as those described above a dye commonly used in such hair tinctorial composition.

Also the cosmetic composition can take the form of a shampoo composition containing the compound according to the present invention admixed with conventional ingredients to this type of composition. Such ingredients are described in "Modern Cosmeticology" Volume 1 pages 378 to 386 (1962) of R. G. HARRY.

These shampoos are clear and their pH can be varied between 4 and 8.5 without changing their appearance.

Also, these shampoos have a conditioning effect on hair which is particularly marked at said pH. They all yield excellent results when used to wash hair.

In order that the invention may be more clearly understood, several illustrative examples will now be described, without limiting the scope of the invention to the details thereof.

EXAMPLE 1

Synthesis of the compound having the formula:

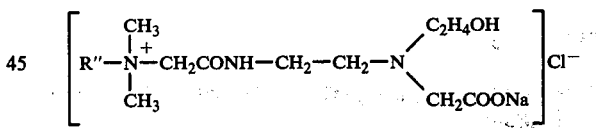

in which R″ represents a cetyl radical.

0.5 mol of dimethyl-cetylamine known under the trademark "Armeen DM 16D" is heated at 90°-95° C. for 1½ hours with 0.5 mol of ethyl monochloroacetate and 40 g of absolute alcohol. Carboethoxymethyl-dimethyl-cetyl-ammonium chloride is obtained.

To this is added, in 30 minutes, 0.5 mol of N-(hydroxyethyl)-ethylene diamine.

Aminolysis begins spontaneously at ambient temperature. It is terminated by heating the mixture to 90° C. for 1½ hours.

The resulting amido-amine, having the formula:

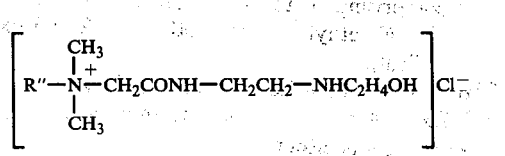

is then condensed with sodium monochloroacetate to form the sodium salt of the corresponding amino-acetic acid.

The condensating reaction is carried out by introducing successively into the solution: first, at a temperature of 10° C, 0.725 mole of crystallized monochloroacetic acid, then 0.725 mol of sodium carbonate to neutralize the hydrochloric acid liberated during the reaction, which lasts 2 hours.

After separation of the sodium chloride and drying by evaporation, a viscous product having the above formula is obtained.

This compound is soluble in either an alkaline or an acid medium.

EXAMPLE 2

Applying the procedure described in Example 1 and replacing the dimethyl cetyl amine by a mixture of dimethylated fatty amines obtained from the fatty acids of copra, a compound having the following formula is prepared:

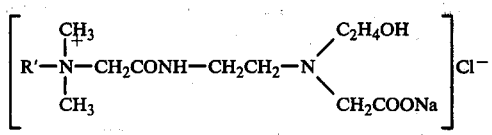

in which R' represents mixtures of alkyl and alkenyl radicals formed from the fatty acid mixture of copra which have 6–18 C atoms.

The term "copra" as R' means those fatty acids having 6–18 C atoms (or R having 5–17 C atoms not including the carboxyl carbon atom) saturated and unsaturated, derived from coconut oil as a mixture, the same being the widely used source of fatty acids for soaps and shampoos. Obviously, other fatty acids and mixtures thereof normally used to manufacture soap are equivalent but copra is preferred.

The usual route to the formation of fatty amines derived from fatty acids of copra is:

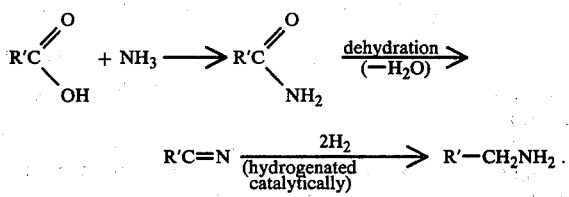

The primary amines are then converted to substituted amines using formaldehyde and formic acid.

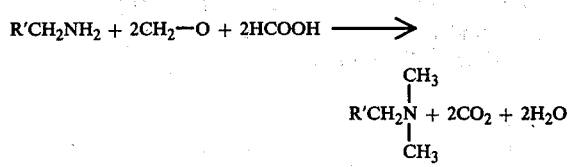

EXAMPLE 3

To prepare the compound having the formula:

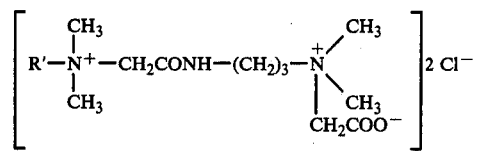

in which R' represents mixtures of alkyl and alkenyl radicals formed from the fatty acids of copra, the following procedure is used:

Carbethoxymethyl-dimethylalkyl-(copra)-ammonium chloride is prepared by heating equimolecular quantities of dimethylated fatty amines obtained from the fatty acids of copra (57.25 g.) and ethyl monochloracetate (30.6 g.) to 75° C. for 3 hours.

To the 86 g. of betainic ester thus obtained are added 25 g. of anhydrous dimethylamino propylamine while stirring at 45° C.

The temperature of the reaction mass rises to 55° C. The mixture is then heated to 60°–70° C. for 7 hours. The percentage of aminolysis calculated from the proportion of the amine functions remaining is about 90%.

To 107 g. of the condensation product thus obtained are added 2.25 g. of a 41.6% aqueous sodium hydroxide solution and 34 g. of ethyl monochloracetate. The temperature of the mixture rises to 60° C.

The mixture is left overnight at the ambient temperature; then an ester having the following formula:

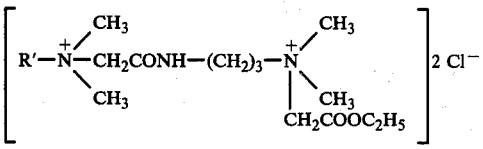

is saponified, using a stoichiometric quantity of concentrated aqueous sodium hydroxide solution.

After separation by filtration of the sodium chloride produced and evaporation of the alcohol, the compound having the above formula is obtained.

It takes the form of a clear yellow paste which dissolves easily in either an alkaline or an acid medium.

EXAMPLE 4

To prepare the compound having the formula:

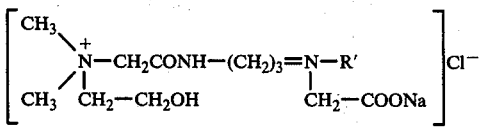

in which R' represents mixtures of alkyl and alkenyl radicals formed from fatty acids of copra, the procedure described in Example 1 is used with the exception that the dimethylated fatty amines are replaced by dimethylaminoethanol and the N-hydroxy-ethylethylenediamine is replaced by an industrial mixture of N- alkyl trimethylene diamines formed from fatty acids of copra.

EXAMPLE 5

The procedure is the same as in Example 1, except that the dimethyl-cetylamine is replaced by a 1-(hydroxyethyl)-2- alkyl imidazoline having the formula:

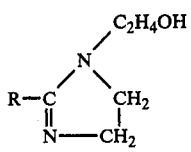

in which R represents mixtures of alkyl and alkenyl radicals obtained from fatty acids of copra having 5–17 C atoms. A compound is then prepared which may be presented by the resonance formulae:

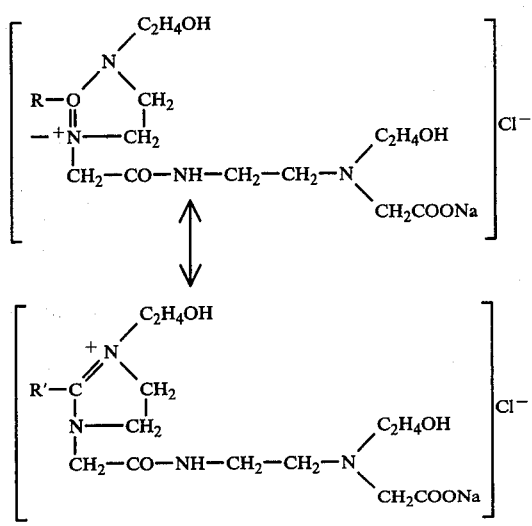

The above imidazoline compounds are made by condensing a fatty acid with ethylene diamine (or derivatives thereof) as follows:

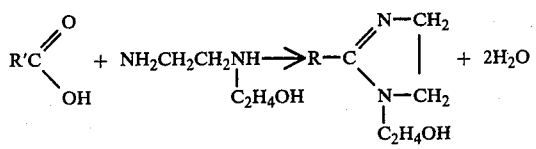

If the preferred copra fatty acids are used in which R' represents a mixture of alkyl and alkenyl radicals having 6–18 C atoms, R represents 5–17 C atoms.

The condensation is carried out in a solvent such as xylene at about 150° C; the reaction being completed upon the formation of a stoichiometric quantity of water.

EXAMPLE 6

To prepare a compound having the formula:

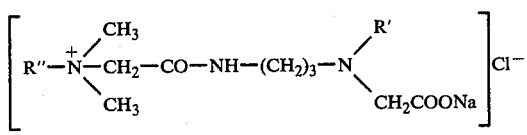

in which R" represents a cetyl radical and R' represents mixtures of alkyl and alkenyl radicals obtained from fatty acids of copra having 6–18 C atoms, carboethoxymethyl-dimethylcetyl-ammonium chloride is aminolyzed by a mixture of N-alkyl-(copra)-trimethylene-diamines obtained from fatty acids of copra. The resulting amidoamine is then condensed with sodium monochloroacetate.

An amphoteric surface-active agent is obtained comprising two lipophile chains per molecule. This compound may be dispersed in water in an alkaline medium. At pH = 6.5 the aqueous solution forms a transparent gel.

EXAMPLE 7

To prepare the compound having the formula:

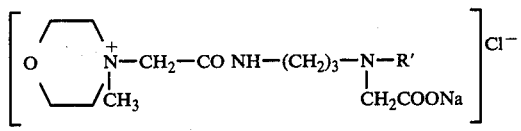

in which R' represents mixtures of alkyl and alkenyl radicals formed from the fatty acids of copra the following procedure is used: 32.5 g of methylchloracetate (0.3 moles) are added at 50° C. to 30 g of methyl morpholine (0.3 mole) in the presence of 10 ml of methanol and by heating 1 h at 50°–55° C. and then precipitating with acetone a compound having the following formula is obtained with a yield at 73%:

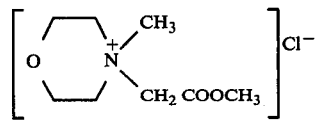

To 21 g (0.1 mole) of this compound are added at 28° C., 29 g (0.1 mole) of a diamine of the formula: NH$_2$—(CH$_2$)$_3$— NH—R' in which R' has the same meaning as above.

The temperature is raised to 50°–60° C. and 10 ml of methanol is then added in order to homogenize the mixture. After one night at room temperature, the methanol is evaporated by heating the mixture in a vacuum. The product obtained is then dissolved in 50 ml of absolute alcohol and 14 g (0.15 mole) of monochloracetic acid is added to a temperature of 10° C. with 15 grams of NaOH at 40% in order to neutralize the monochloracetic acid.

The temperature is raised progressively up to 60° C. and then 15 g of NaOH at 40% is again added drop by drop.

The mixture is heated at reflux temperature for 45 minutes - 1 hour and filtered in order to eliminate the salts. The alcohol is then evaporated under vacuum and it is obtained an oily product which is soluble in water which is slightly acid or slighty basic.

EXAMPLE 8

The following tinctorial composition is prepared: compound having the following formula obtained according to Example 6:

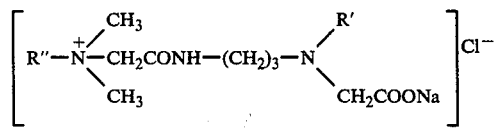

| | |
|---|---|
| in which R'' represents a cetyl radical and R' is the same as above indicated | 5 g |
| lauric alcohol oxyethylenated with 20 molecules of ethylene oxide | 6 g |
| diethanolamide of fatty acids of copra | 4 g |
| 1-amino-2-nitro-4-methylamino benzene | 0.5 g |
| crystallized citric acid | 0.4 g |
| water, q.s.p. | 100 g |

The pH of this compound is 6.5.

It takes the form of a thick, transparent liquid.

This product, applied to clean light chestnut hair which has been dampened and dried with a towel, yields, after a 10 minute pause, rinsing and drying, violine glints. The hair is shiny, supple and easy to comb out.

EXAMPLE 9

The following tinctorial composition is prepared:
compound having the following formula obtained according to Example 4, at a 49% concentration:

$$\left[ \begin{array}{c} CH_3 \\ \diagdown \\ N \\ \diagup \\ CH_3 \end{array} \begin{array}{c} CH_2-CONH-(CH_2)_3-N \\ | \\ CH_2-CH_2-OH \end{array} \begin{array}{c} R' \\ \diagup \\ \diagdown \\ CH_2-COONa \end{array} \right] Cl^-$$

| | |
|---|---|
| in which R' represents mixtures of alkyl and alkenyl radical derived from fatty acids of copra | 6 g |
| lauric alcohol oxyechylenated with 20 molecules of ethylene oxide | 6 g |
| copra diethanolamide | 3 g |
| 1-hydroxy-2,5-diamino-4-methyl benzene hydrochloride | 1.5 g |
| 1-hydroxy-2-amino-4-methylamino benzene sulfate | 1.25 g |
| 40% sodium bisulfite solution | 1.32 g |
| 5N sodium hydroxide solution | 1 cm 3 |
| water, q.s.p. | 100 g |

A clear, foaming product is obtained.

This product washes and dyes at the same time.

Applied like a shampoo to brown hair which is as much as 30% white, it covers the white hair well after a 20 minute pause, rinsing, and drying. The whole coiffure is brown with bluish glints.

All of the following Examples describe formulas for shampoos using the new compounds according to the invention.

EXAMPLE 10

The following solution is prepared:
compound having the following formula, obtained as in Example 4:

$$\left[ \begin{array}{c} CH_3 \\ \diagdown \\ N \\ \diagup \\ CH_3 \end{array} \begin{array}{c} -CH_2CONH-(CH_2)_3-N-R' \\ | \\ CH_2-CH_2OH \end{array} \begin{array}{c} \\ | \\ CH_2COONa \end{array} \right] Cl^-$$

| | |
|---|---|
| in which R' is the same as above | 10 g |
| lactic acid, q.s.p. pH = 4 | |
| water, q.s.p. | 100 cc |

EXAMPLE 11

The following solution is prepared:
compound having the following formula, obtained as in Example 4: (Sodium monochloroacetate being replaced by potassium monochloracetate)

$$\left[ \begin{array}{c} CH_3 \\ \diagdown \\ N \\ \diagup \\ CH_3 \end{array} \begin{array}{c} -CH_2CONH-(CH_2)_3-N-R' \\ | \\ CH_2-CH_2OH \end{array} \begin{array}{c} \\ | \\ CH_2COOK \end{array} \right] Cl^-$$

| | |
|---|---|
| in which R' is the same as above | 10 g |
| lactic acid, q.s.p. pH = 8.5 | |
| water, q.s.p. | 100 cc |

EXAMPLE 12

The following solution is prepared:
compound having the following formula, obtained according to Example 4:

$$\left[ \begin{array}{c} CH_3 \\ \diagdown \\ N \\ \diagup \\ CH_3 \end{array} \begin{array}{c} -CH_2CONH-(CH_2)_3-N-R' \\ | \\ CH_2-CH_2OH \end{array} \begin{array}{c} \\ | \\ CH_2COONa \end{array} \right] Cl^-$$

| | |
|---|---|
| in which R' is the same as above | 4 g |
| polyethoxylated lauric alcohol (with 12 molecules of ethylene oxide) | 9 g |
| lactic acid, q.s.p. pH = 4 | |
| water, q.s.p. | 100 cc |

EXAMPLE 13

The following solution is prepared:
compound having the following formula, obtained according to Example 4:

$$\left[ \begin{array}{c} CH_3 \\ \diagdown \\ N \\ \diagup \\ CH_3 \end{array} \begin{array}{c} -CH_2CONH-(CH_2)_3-N-R' \\ | \\ CH_2-CH_2OH \end{array} \begin{array}{c} \\ | \\ CH_2COONa \end{array} \right] Cl^-$$

| | |
|---|---|
| in which R' is the same as above | 4.5 g |
| polyethoxylated nonylphenol (with 10 molecules of ethylene oxide) | 8 g |
| lactic acid, q.s.p. pH = 5 | |
| water, q.s.p. | 100 cc |

EXAMPLE 14

The following solution is prepared:
compound having the following formula obtained as in Example 4:

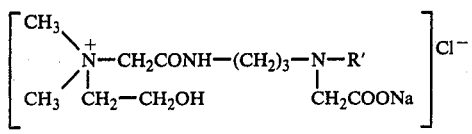

in which R' is the same as above     2 g compound having the following formula:

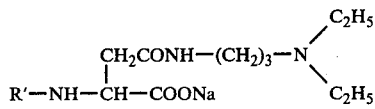

| in which R' is the same as above | 2 g |
|---|---|
| lauric alcohol oxyethylenated with 12 molecules of ethylene oxide | 8 g |
| lactic acid, q.s.p. pH = 6 | |
| water, q.s.p. | 100 cc |

EXAMPLE 15

The following solution is prepared:
compound having the following formula, obtained as in Example 7:

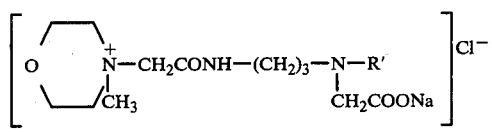

| in which R' is the same as above | 4 g |
|---|---|
| lauric alcohol oxyethylenated with 12 molecules of ethylene oxide | 7 g |
| lauric diethanolamide | 1 g |
| lactic acid, q.s.p. pH = 7 | |
| water, q.s.p. | 100 cc |

EXAMPLE 16

The following solution is prepared:
compound having the following formula, obtained as in Example 4:

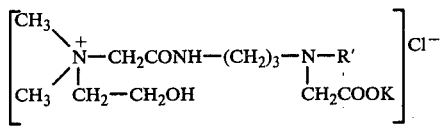

in which R' is the same as above     6 g compound having the following formula, obtained as in Example 2: (sodium monochloroacetate being replaced by potassium monochloroacetate)

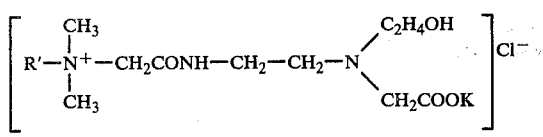

| in which R' is the same as above | 4 g |
|---|---|
| lactic acid, q.s.p. pH = 5 | |

| water, q.s.p. | 100 cc |
|---|---|

EXAMPLE 17

The following solution is prepared:
compound having the following formula, obtained as in Example 4:

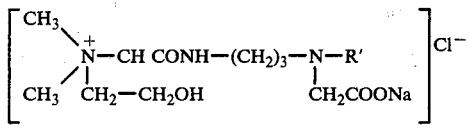

| in which R' is the same as above | 1 g |
|---|---|
| lauryl ammonium sulfate | 9 g |
| lauric diethanolamide | 0.8 g |
| lactic acid, q.s.p. pH = 7 | |
| water, q.s.p. | 100 cc |

EXAMPLE 18

The following solution is prepared:
compound having the following formula, obtained as in Example 4:

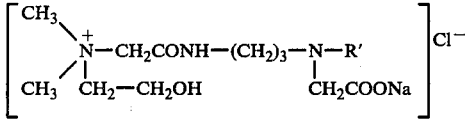

| in which R' is the same as above | 3 g |
|---|---|
| lauryl ammonium sulfate | 9 g |
| lauric diethanolamide | 1 g |
| lactic acid, q.s.p. pH = 7 | |
| water, q.s.p. | 100 cc |

This compound is clear but rather viscous. Its viscosity is:
  355 centipoises at pH = 4
  372 centipoises at pH = 7
  630 centipoises at pH = 8.5

EXAMPLE 19

The following solution is prepared:
compound having the following formula, obtained as in Example 4:

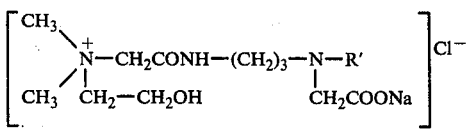

in which R' is the same as above     5 g compound having the following formula, obtained as in Example 3:

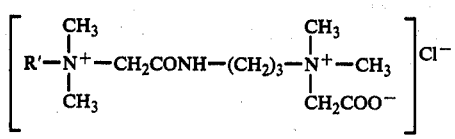

| in which R' is the same as above | 5 g |
| --- | --- |
| lactic acid, q.s.p. pH = 6 | |
| water, q.s.p. | 100 cc |

EXAMPLE 20

The following solution is prepared:
compound having the following formula, obtained as in Example 4:

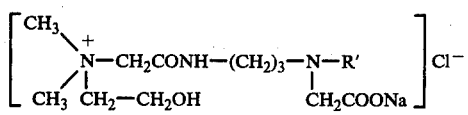

in which R' is the same as above     2.5 g compound having the following formula, obtained as in Example 3:

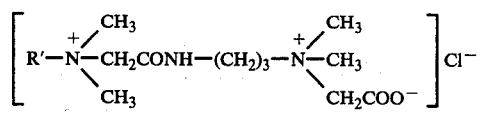

| in which R' is the same as above | 1.5 g |
| --- | --- |
| lauric alcohol polyethoxylated with 12 molecules of ethylene oxide | 7 g |
| lauric diethanolamide | 0.8 g |
| lactic acid, q.s.p. pH = 5 | |
| water, q.s.p. | 100 cc |

EXAMPLE 21

The following solution is prepared:

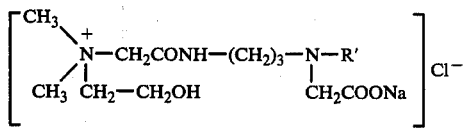

| in which R' is the same as above | 3 g |
| --- | --- |
| compound obtained as in Example 5 | 2 g |
| nonylphenol oxyethylenated with 10 molecules of ethylene oxide | 7.5 g |
| lactic acid, q.s.p. pH = 5 | |
| water, q.s.p. | 100 cc |

EXAMPLE 22

The following solution is prepared:
compound having the following formula, obtained as in Example 4:

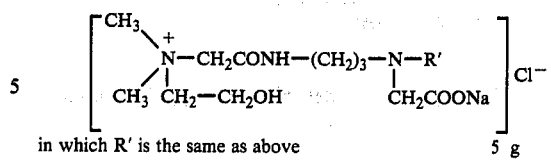

in which R' is the same as above     5 g compound having the following formula, obtained as in Example 6:

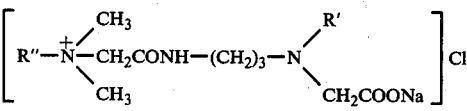

| in which R" represents a cetyl radical and R' is the same as above | 5 g |
| --- | --- |
| lactic acid, q.s.p. pH = 4 | |
| water, q.s.p. | 100 cc |

This compound takes the form of a thin gel. Its viscosity is 285 centipoises.

EXAMPLE 23

The following solution is prepared:
compound having the following formula, obtained as in Example 4:

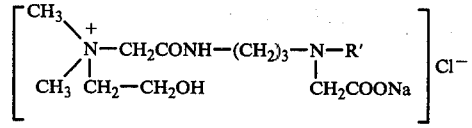

in which R' is the same as above     3.5 g compound having the following formula, obtained as in Example 6:

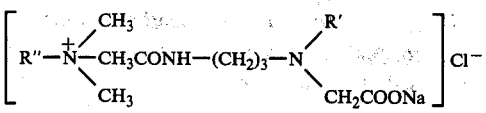

| in which R" represents a cotyl radical and R' is the same as above | 2 g |
| --- | --- |
| lauric alcohol oxylthylenated with 12 molecules of ethylene oxide | 7 g |
| lactic acid, q.s.p. pH = 4 | |
| water, q.s.p. | 100 cc |

EXAMPLE 24

The following solution is prepared:
compound according to Example 5:
compound having the following formula obtained as in Example 4:

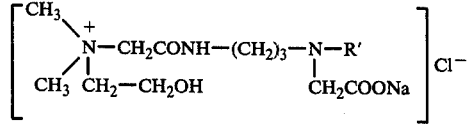

-continued in which R' is the same as above    2.5 g compound according to Example 6, having the formula:

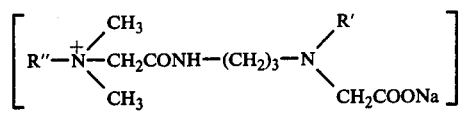

| in which R″ represents a cetyl radical and R' is the same as above | 2 g |
| --- | --- |
| lauric alcohol oxyethylenated with 12 molecules of ethylene oxide | 8 g |
| lauric diethanolamide | 0.8 g |
| lactic acid, q.s.p. pH = 6 | |
| water, q.s.p. | 100 cc |

What is claimed is:

1. A chemical compound having the formula:

in which:

$n$ is a whole number equal to 2 or 3;

$A^+$ represents an aliphatic tertiary amine corresponding to the formula:

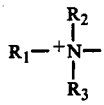

wherein $R_1$ is a radical selected from the group consisting of methyl, cetyl and a radical derived from copra fatty acid having 6–18 carbon atoms;

$R_2$ and $R_3$ can be the same or different and represent a radical selected from the group consisting of alkyl and hydroxyalkyl radicals having 1 to 3 carbon atoms;

B is a radical corresponding to the formula:

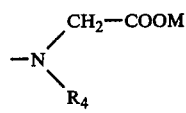

in which $R_4$ is selected from the group consisting of alkyl and hydroxyalkyl radicals having 1–3 carbon atoms and a radical derived from copra fatty acids having 6–18 carbon atoms;

M represents an alkali metal selected from the group consisting of potassium and sodium; and $X^-$ is a halide ion.

2. Compound according to claim 1 having the following formula:

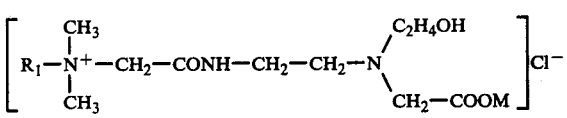

in which $R_1$ is a radical derived from copra fatty acid having 6–18 carbon atoms and M is selected from the group consisting of potassium and sodium.

3. Compound according to claim 1 having the following formula:

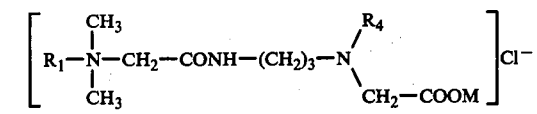

in which $R_4$ is a radical derived from copra fatty acid having 6–18 carbon atoms;

$R_1$ is selected from the group consisting of methyl and cetyl radicals;

$R_3$ is selected from the group consisting of hydroxyethyl and methyl, with the proviso that $R_1$ is cetyl when $R_3$ is methyl; and M is selected from the group consisting of sodium and potassium.

* * * * *